(12) United States Patent
Wu

(10) Patent No.: US 7,329,313 B2
(45) Date of Patent: Feb. 12, 2008

(54) AIR CLEANER

(75) Inventor: Kashing Wu, Hong Kong (HK)

(73) Assignee: Chiaphua Industries Limited, Hong Kong Sar (HK)

( * ) Notice: Subject to any disclaimer, the term of this patent is extended or adjusted under 35 U.S.C. 154(b) by 152 days.

(21) Appl. No.: 10/540,932

(22) PCT Filed: Dec. 30, 2002

(86) PCT No.: PCT/CN02/00951

§ 371 (c)(1),
(2), (4) Date: Dec. 16, 2005

(87) PCT Pub. No.: WO2004/059218

PCT Pub. Date: Jul. 15, 2004

(65) Prior Publication Data

US 2006/0130656 A1    Jun. 22, 2006

(51) Int. Cl.
  *B01J 19/12*   (2006.01)
  *B01D 46/00*   (2006.01)
  *A61L 2/10*    (2006.01)

(52) U.S. Cl. .................. 96/224; 422/24; 422/186.3

(58) Field of Classification Search ................ 96/224, 96/16; 422/24, 186.3
See application file for complete search history.

(56) References Cited

U.S. PATENT DOCUMENTS

| | | | | |
|---|---|---|---|---|
| 5,833,740 A | * | 11/1998 | Brais ............................. 96/16 |
| 5,891,399 A | * | 4/1999 | Owesen ....................... 422/121 |
| 5,997,619 A | * | 12/1999 | Knuth et al. .................. 96/224 |
| 6,053,968 A | * | 4/2000 | Miller .......................... 96/224 |
| 6,322,614 B1 | * | 11/2001 | Tillmans ........................ 96/16 |
| 6,752,970 B2 | * | 6/2004 | Schwartz et al. ......... 422/186.3 |
| 6,761,859 B1 | * | 7/2004 | Oda ......................... 422/186.3 |
| 6,783,578 B2 | * | 8/2004 | Tillman, Jr. .................. 96/224 |
| 6,875,988 B1 | * | 4/2005 | Sauska et al. ......... 250/455.11 |
| 6,939,397 B2 | * | 9/2005 | Nelsen et al. ................ 96/224 |
| 7,175,814 B2 | * | 2/2007 | Dionisio ..................... 422/121 |
| 2003/0021721 A1 | * | 1/2003 | Hall ............................. 422/4 |
| 2004/0245164 A1 | * | 12/2004 | Sellner et al. ........... 210/323.2 |
| 2005/0016378 A1 | * | 1/2005 | Yuen ............................. 96/16 |
| 2006/0219235 A1 | * | 10/2006 | Bagwell et al. ......... 126/299 R |

* cited by examiner

*Primary Examiner*—Duane Smith
*Assistant Examiner*—Robert A Clemente
(74) *Attorney, Agent, or Firm*—Leydig, Voit & Mayer, Ltd.

(57) ABSTRACT

An air cleaner includes a housing, a filter, a photocatalyst reaction unit which can form spiral a air flow, a forced convection device, and an electrocircuit controller. The forced convection device is located between the filter and the photocatalyst reaction unit. Because the air cleaner uses a longitudinal air conduit, an air inlet along a tangential direction of the air conduit and spiral guide vanes at the inlet, air passing through a fan and into the air conduit flows spirally in the conduct conduit to increase the time during which air contacts the photocatalyst and enables the light of the ultraviolet lamp to radiate the photocatalyst directly so that the cleaning efficiency of the photocatalyst is increased.

5 Claims, 2 Drawing Sheets

AIR CLEANER

FIELD OF THE INVENTION

The present invention relates to an air cleaning device using photocatalyst, more particularly, to an air cleaning device which has combined effects of sterilization, air filtering and purifying.

DESCRIPTION OF THE RELATED ART

The air cleaning device has been increasingly and widely used as a good varieties of pollution are brought about in the modern society. The air cleaning device typically includes a cooling device, an air purifying device and an exhaust fan etc. In a conventional air purifying device, a corrugated paper material is commonly used as a means for separating fume or dust so as to purify the air. Further, active carbon is added in the air cleaning device so that the air is further filtered. That is, the air laden with bacteria can be absorbed by the active carbon contained in the air cleaning device. However, the above conventional air cleaning device is problematic in that the active carbon must be replaced when it is saturated with contaminants removed from the air. More often than not, the consumer may neglect to replace the active carbon. Accordingly, air filtered by the air cleaning device in which the active carbon has not been replaced is not effectively improved in quality.

In recent years, photocatalyst which is mainly composed of $TiO_2$ has been proposed. The photocatalyst generates a catalyst reaction upon radiation of minute ultra-violet ray so that sterilization and deodorization effects on the air laden with bacteria are achieved. In an air cleaning device in which photocatalyst of $TiO_2$ is applied, a matrix with a complex structure shaped like a honeycomb or a woven web cloth is employed and the matrix or the woven web cloth is impregnated with or sprayed with photocatalyst of $TiO_2$. However, the above two kinds of conventional air cleaning device have the following disadvantages. For the former one, it is disadvantageous in complicated structure and high cost. For the latter one, it is necessary for the web cloth to be manually cut by the workers. As the specification for the cloth differs from each other in different applications, mass production of the web cloth can not be effected. As a result, no commercialized product of the above air cleaning device is available till now.

Another air cleaning device has been proposed in the Chinese Utility Model Patent No. 00263712.X (Publication No. CN2457491Y). The air cleaning device disclosed in the above utility model publication is configured as follows. More specifically, the air cleaning device includes a body having an air inlet port and an air outlet port. An active carbon filtering material is disposed adjacent the air inlet port inside the body. The air cleaning device further includes a filtering web. Upon operation of the suction fan, the air is drawn into the air cleaning device through the air inlet port and the air filtered by the active carbon filtering material is sucked and thereafter exhausted outside through the air outlet port. The filtering web is configured to be a structure consisting of plastic web layers which are laminated one by one and are manufactured by injection molding process. Each web layer is provided with a plurality of separation ribs and bore holes. The photocatalyst is provided on the separation ribs. Upon radiation of ultra violet ray, the photocatalyst provided on the separation ribs generates a catalyst reaction so as to decompose air, thus achieving effect of sterilization. As described above, as the filtering web is configured to be a structure consisting of plastic web layers which are laminated one by one, in which each web layer is provided with a plurality of separation ribs and bore holes, and the photocatalyst is provided on the separation ribs, it is possible to achieve mass production of the air cleaning device with above arrangements while reducing the cost of it. Furthermore, the air flowing through the bore holes and gaps therebetween gets into contact with the photocatalyst of $TiO_2$ so that a sterilization effect and a deodorization effect are achieved. However, it is an important factor for carrying out the catalyst effect that a sufficient amount of ultra violet ray is incident on photocatalyst and the air to be treated must be brought into contact with the photocatalyst. However, as the carrier of the catalyst of the air cleaning device is configured to be a web-layering shape, the light is not evenly incident on the catalyst. Further, the time in which the air contacts with the catalyst is short and the chance for the contact is relatively low. As a result, the purifying efficiency of the photocatalyst is not satisfactory.

SUMMARY OF THE INVENTION

The present invention has been made to overcome one or more aspects of the above disadvantages in the prior arts. Accordingly, it is an object of the present invention to provide an air cleaning device using photocatalyst in which the chance and time for which the air contacts with the catalyst and the catalytical effect are effectively enhanced and the air purifying efficiency of the catalyst reaction is remarkably increased.

Additional aspects and advantages of the invention will be set forth in part in the description that follows, and in part, will be obvious from the description, or may be learned by the practice of the invention.

The forgoing and other aspects of the present invention are achieved by providing an air cleaning device, comprising: a body; a first filter unit; a photocatalyst reaction unit which can generate spiral air current; a forcible convection unit and a circuit control unit which can adjustably control the operation of the forcible convection unit, wherein: the first filter unit is disposed below the body and has a front surface in shape of an opening so as to communicate with the outside and a rear surface in communication with the forcible convection unit, and the forcible convection unit is disposed between the first filter unit and the photocatalyst reaction unit so as to communicate the first filter unit with the photocatalyst reaction unit, characterized in that:

the photocatalyst reaction unit includes an air duct, a photocatalyst coating layer provided on an interior wall of the air duct, two lamp holders, at least one ultra violet ray tube mounted on the two lamp holders, and a blow guide holder on which a spiral blow guide blade is mounted, wherein two ends of the air duct are hermetically connected to left and right side plates of the body respectively, the air duct is provided at a left side thereof with an air inlet port which is in communication with the air outlet port of the forcible convection unit in a tangential direction thereof and provided at the right side thereof with an air outlet port in a tangential direction thereof;

two ends of each ultra violet ray tube are mounted on the lamp holders and are axially disposed inside the air duct;

the blow guide holder is provided on the left side plate and located at a position of the air inlet port of the air duct;

one of the two lamp holders is connected to the right side plate of the body, and the other one is connected to the blow guide holder.

According to the present invention, a photocatalyst reaction unit in which an elongated air duct is combined with an air inlet port disposed in a tangential direction of the air duct and spiral guide blades disposed at the air inlet port thereof is employed. The air drawn into the air duct through the blower flows spirally inside the air duct along the interior wall of the air duct. As a result, the time and chance for which the air contacts with the photocatalyst are greatly increased.

With this construction, ultra violet ray emitted from the ultra violet ray tube can be directly incident onto the photocatalyst without blocking so that the catalyst reaction effect is greatly enhanced. Thus, the purifying efficiency of the air cleaning device is further increased. Particularly, since the specific gravity of the volatile organic chemical (VOC) and bacteria is greater than that of the air, the volatile organic chemical (VOC) and bacteria will be certainly thrown against the interior wall of the air duct when the air rotates around the central axis of the air duct due to the eccentric forces applied thereupon. In this way, the volatile organic chemical (VOC) and bacteria will come more closely to the photocatalyst. Consequently, the photocatalyst causes the volatile organic chemical (VOC) and bacteria to be decomposed into free ion radicals so that the effects of sterilization, deodorization and purification of air can be achieved.

The air cleaning device of the present invention has a simple construction and can be easily effected with good applicability. The air cleaning device according to the present invention can be widely used as a purifying device in rooms inside a house, automobiles or a good variety of appliances such as air conditioners and dishwashers for dust-removing, sterilization, and air-cleaning.

BRIEF DESCRIPTION OF THE DRAWINGS

The above and other objects and advantages of the invention will become apparent and readily appreciated from the following description of the preferred embodiments, taken in conjunction with the accompanying drawings, in which.

DETAILED DESCRIPTION OF THE PREFERRED EMBODIMENTS

Figure 1:
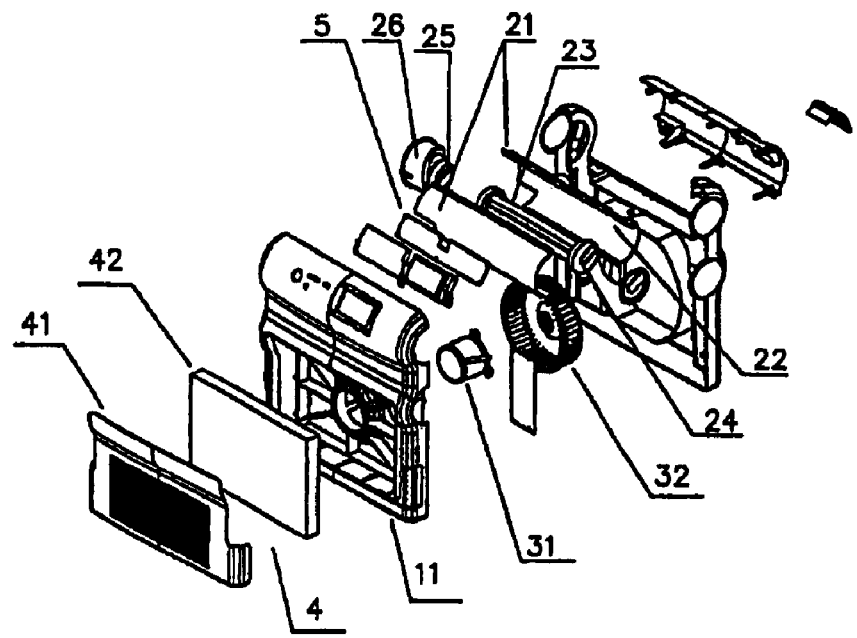
FIG. 1 is an exploded view showing an air cleaning device according to an embodiment of the present invention.

A preferred embodiment of the present invention will be described hereinafter in detail with reference to the attached drawings, wherein the like reference numerals refer to the like elements throughout the specification. The present invention may, however, be embodied in many different forms and should not be construed as being limited to the embodiment set forth herein; rather, this embodiment is provided so that the present disclosure will be thorough and complete, and will fully convey the concept of the invention to those skilled in the art.

Figure 2:
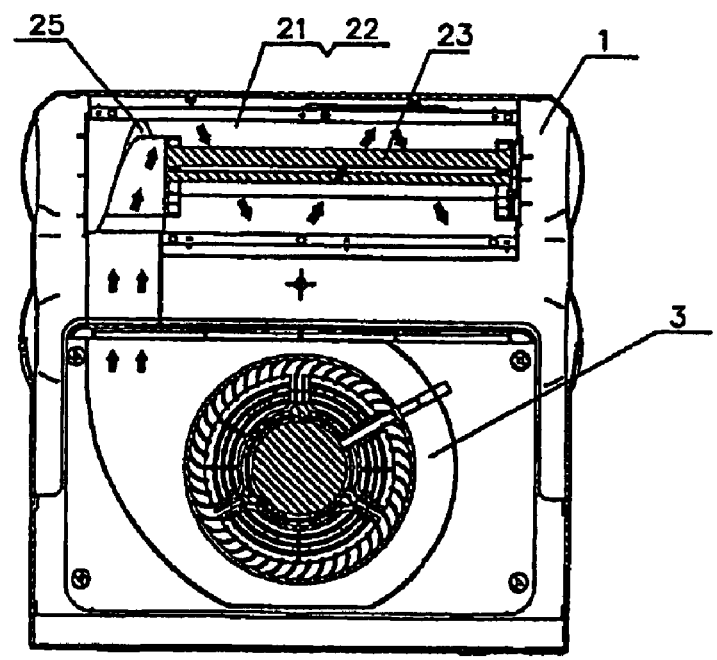
FIG. 2 is sectional view of an air cleaning device according to an embodiment of the present invention.
Figure 3:
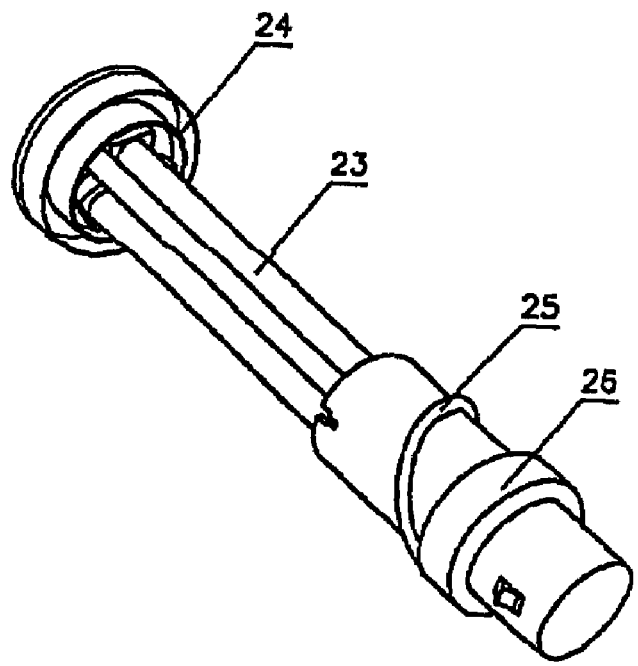
FIG. 3 is a schematic view showing the construction of a lamp holder and an ultra violet ray tube of the present invention.
Figure 4:
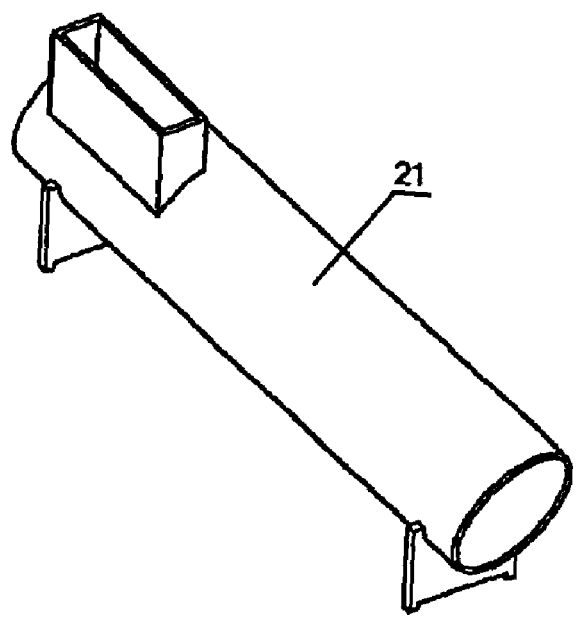
FIG. 4 is a schematic view showing the construction of the air duct of the present invention.

As shown in FIGS. 1-4, the air cleaning device of the present invention includes a body 1, a first filter unit 4 for filtering the air so as to remove contaminants and dust from the air, a photocatalyst reaction unit which generates spiral air current; a forcible convection unit 3 which forcibly draws air from outside into the first filter unit 4 and sends it into the photocatalyst reaction unit, and a circuit control unit 5 which can adjustably control the operation of the forcible convection unit 3. The first filter unit 4 is disposed below the body 1, having a front surface in shape of an opening so as to communicate with the outside and a rear surface in communication with an inlet port of the forcible convection unit 3. The forcible convection unit 3 is disposed between the first filter unit 4 and the photocatalyst reaction unit so as to communicate the first filter unit 4 with the photocatalyst reaction unit. The air which has been filtered by the first filter unit 4 is delivered into the photocatalyst reaction unit so that the catalyst reaction is carried out therein. The circuit control unit 5 is provided inside the body 1, and a plurality of control buttons and a display unit are provided on a control panel of the body 1. With this construction, the operations of the photocatalyst reaction unit and the forcible convection unit 3 can be adjustably controlled by manipulation of the buttons provided on the control panel of the body 1.

The first filter unit 4 includes a dust blocking web 42 which is provided on a front housing 11 of the body 1 and a movable door 41. The dust blocking web 42 is a filter web made of active carbon or high-efficiency HEPA filtering materials or a combination thereof. The movable door 41 is disposed on the front side of the dust blocking web 42 and provided with an air suction grill. The forcible convection unit 3 is configured to be a blower consisting of a motor 31 which is provided between a front housing and a rear housing of the body 1 and connected to the circuit control unit 5, and a plurality of blades 32 which are mounted on a rotation shaft of the motor 31. An air inlet port of the blower is in communication with the first filter unit 4 and an air outlet port thereof is in communication with an air inlet port of the photocatalyst reaction unit. In order to effectively generate spiral air current, the photocatalyst reaction unit includes an elongated air duct 21, a photocatalyst coating layer 22 disposed on an interior wall of the air duct 21, two lamp holders 24, at least one ultra violet ray tube 23 mounted on the two lamp holders 24 and a blow guide holder 26 on which a spiral blow guide blade 25 is mounted. The air duct 21 is composed of two elongated housings each having a semi-circle section which can be abutted with each other. A recess is provided on the lower left side of each of the two semi-circle shaped housings. Accordingly, the recesses provided on the two semicircle shaped housings respectively can be abutted with each other so as to form an air inlet port. An air outlet port is provided on a right end of the sidewall of one of the semi-circle shaped housing.

The interior wall of the air duct 21 can be a smooth surface or a surface with undulations. In an embodiment of the present invention, the interior wall of the air duct 21 is a surface with undulations. The photocatalyst coating layer 22 is coated onto the surface of the interior wall of the air duct by a spraying or impregnating process. Consequently, the ratio surface area of the photocatalyst coating layer can be effectively increased so that the purifying efficiency can be enhanced. Two ends of the air duct 21 are hermetically connected to left and right side plates of the body 1. The air duct is provided at the left side thereof with an air inlet port which is in communication with the air outlet port of the forcible convection unit in a tangential direction thereof. In this way, since the air inlet port of the air duct is inclined and the air inlet port is disposed in a tangential direction of the air duct 21, the air drawn into the air duct 21 can reliably flow along the interior wall of the air duct 21 so as to enhance the contact between the air and the photocatalyst only by adjusting the blowing speed of the forcible convection unit 3.

In this case, three ultra violet ray tubes 23 are arranged in form of a Chinese Character "品". Two ends of each ultra violet ray tube 23 are mounted on the lamp holders 24 and are axially disposed inside the air duct 21. With this construction, ultra violet ray emitted from the ultra violet ray tube 23 can be directly incident onto the photocatalyst without blocking so that the catalyst reaction is enhanced into the most desirable state. Thus, the purifying efficiency of the air cleaning device is further increased.

The blow guide holder 26 on which a spiral blow guide blade 25 is mounted is provided on the left side plate of the body 1 and located at a position of the air inlet port of the air duct 21. Due to rotation of the blow guide blade 25, the air flows spirally inside the air duct 21. As a result, the time and the chance for which the air contacts with the photocatalyst are improved, thus enhancing purifying efficiency of the air cleaning device of the present invention.

In addition, one of the two lamp holders 24 is connected to the right side plate of the body 1, and the other one is connected to the blow guide holder 26. With this construction, the lamp holders, the ultra violet ray tubes, the blow guide holder and the air duct are integrally formed into a single assembly.

The invention claimed is:

1. An air cleaning device with a photocatalyst, comprising:
    a body;
    a filter unit;
    a photocatalyst reaction unit which can generate a spiral air current;
    a forcible convection unit; and
    a circuit control unit which can adjustably control operation of the forcible convection unit, wherein
       the filter unit is disposed below the body and has a front surface with an opening communicating with the outside and a rear surface in communication with the forcible convection unit,
       the forcible convection unit is disposed between the filter unit and the photocatalyst reaction unit so the filter unit communicates with the photocatalyst reaction unit,
       the photocatalyst reaction unit includes an air duct, a photocatalyst coating layer disposed on an interior wall of the air duct, two lamp holders at least one ultra violet ray tube mounted on the two lamp holders, and a blow guide holder on which a spiral blow guide blade is mounted,
       ends of the air duct are hermetically connected to left and right side plates of the body, respectively,
       the air duct includes, at a left side, an air inlet port in communication with air outlet port of the forcible convection unit, in a tangential direction thereof, at a right side thereof, and with an air outlet port in a tangential direction thereof,
       ends of each ultra violet ray tube are mounted on the lamp holders and axially disposed inside the air duct, respectively;
       the blow guide holder is located on the left side plate and located at a position of the air inlet port of the air duct, and
       one of the two lamp holders is connected to the right side plate of the body and the other lamp holder is connected to the blow guide holder.

2. The air cleaning device with a photocatalyst according to claim 1, wherein the air duct includes two elongated housings, each housing having a semi-circle section, which can be abutted with each other, wherein each of the two semi-circle shaped housings includes at a lower left side, a recess so that the recesses of the two housings can be abutted with each other so as to form the air inlet port.

3. The air cleaning device with a photocatalyst according to claim 1, wherein
    the interior wall of the air duct includes a surface with undulations, and
    the photocatalyst coating layer coats the surface with undulations of the interior wall of the air duct.

4. The air cleaning device with a photocatalyst according to claim 1, wherein
    the filter unit includes a dust blocking web and a movable door on a front housing of the body,
    the dust blocking web is a filter web made of active carbon or high-efficiency HEPA filtering materials or a combination thereof, and
    the movable door is disposed on a front side of the dust blocking web and includes an air suction grill.

5. The air cleaning device with a photocatalyst according to claim 1, wherein
    the forcible convection unit includes a blower having a motor located between a front housing and a rear housing of the body and connected to the circuit control unit, and a plurality of blades mounted on a rotating shaft of the motor, and
    an air inlet port of the blower is in communication with the filter unit and an air outlet port of the filter unit is in communication with an air inlet port of the photocatalyst reaction unit.

* * * * *